United States Patent [19]

Griggs et al.

[11] Patent Number: 4,811,736
[45] Date of Patent: Mar. 14, 1989

[54] SURGICAL DRILL AND BUR FOR USE THEREWITH

[75] Inventors: Calvin Griggs; J. C. Horn, both of Memphis, Tenn.

[73] Assignee: Treace Medical, Inc., Memphis, Tenn.

[21] Appl. No.: 40,138

[22] Filed: Apr. 20, 1987

[51] Int. Cl.⁴ .............................................. A61B 17/32
[52] U.S. Cl. .................................................. 128/305.1
[58] Field of Search ...................... 128/305.1, 310, 305; 408/226

[56] References Cited

U.S. PATENT DOCUMENTS

| | | | |
|---|---|---|---|
| 1,984,839 | 12/1934 | Murray | 279/1 TS |
| 2,606,366 | 8/1952 | Stevens . | |
| 2,878,809 | 3/1959 | Treace | 128/305.1 X |
| 2,905,178 | 9/1959 | Hilzinger, III . | |
| 3,193,335 | 7/1965 | Wing . | |
| 4,071,029 | 1/1978 | Richmond et al. | 728/310 X |
| 4,134,705 | 1/1979 | Smith | 408/112 |
| 4,445,509 | 5/1984 | Auth | 128/305 |

FOREIGN PATENT DOCUMENTS 540158 11/1931 Fed. Rep. of Germany .

Primary Examiner—Michael H. Thaler
Attorney, Agent, or Firm—Bell, Seltzer, Park & Gibson

[57] ABSTRACT

A surgical drill is disclosed which includes an electric motor and an elongate tubular support sleeve. A drill bur is mounted so as to extend through the support sleeve and extend outwardly from the free end thereof, and the bur includes a shaft which mounts a plastic sleeve bearing for relative rotation therewith. The bearing contacts the internal bore of the support sleeve, so as to provide a seal therebetween which prevents the passage of debris past the bearing and into the support sleeve. Also, a portion of the plastic sleeve bearing is visible during use, and the bearing includes a distinctive color which is correlated to the particular configuration or size of the cutting tip of the bur, to thereby facilitate its identification during use of the drill.

7 Claims, 1 Drawing Sheet

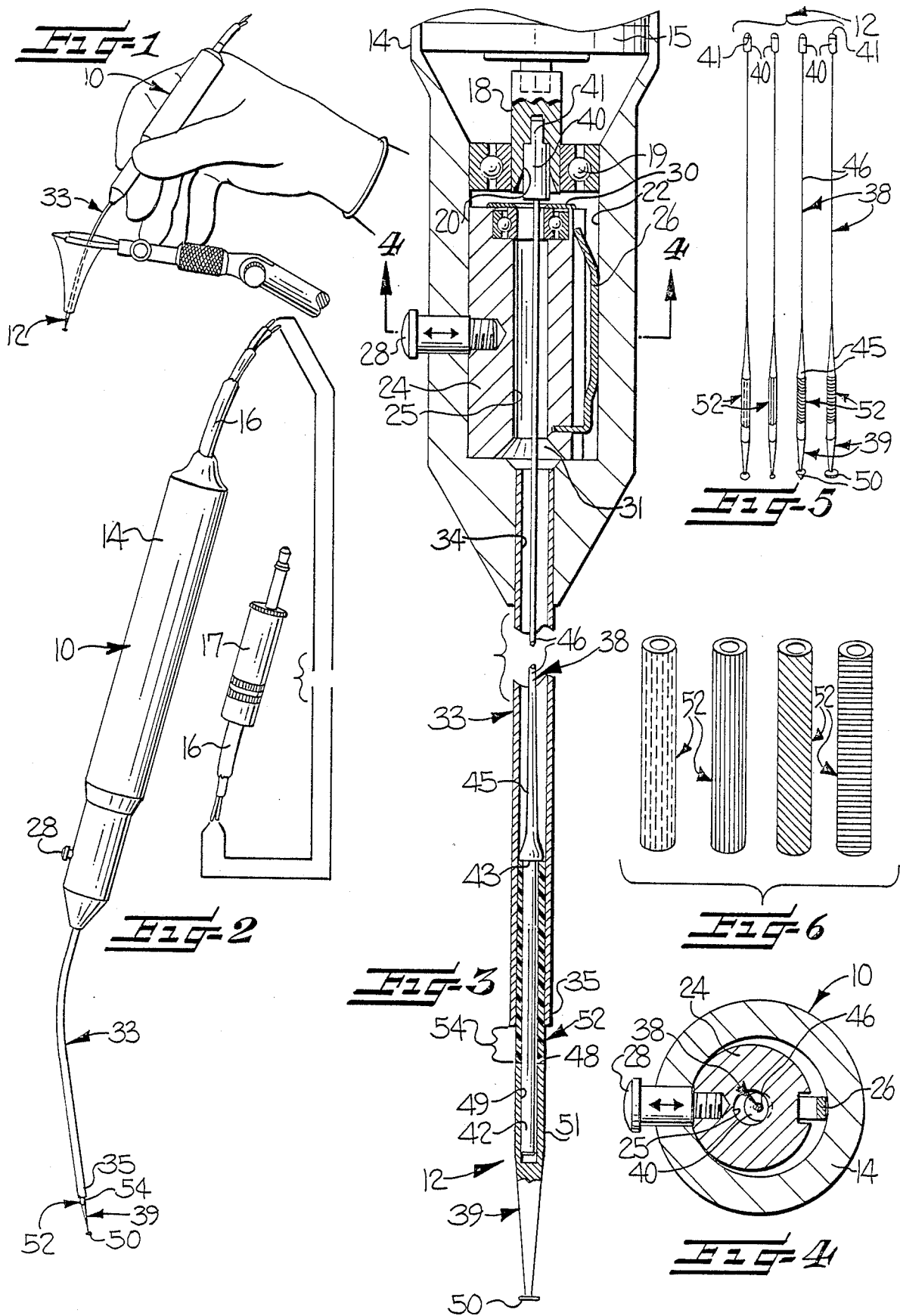

SURGICAL DRILL AND BUR FOR USE THEREWITH

BACKGROUND OF THE INVENTION

The present invention relates to a surgical drill of the type commonly used for performing otological surgery in the middle ear, and to a novel bur or bit adapted for use with such a drill.

In performing otological surgery, it is common to employ a drill which comprises a small handpiece which houses an electric motor and a chuck, with the chuck being rotated by the motor under the control of a foot operated switch. The forward end of the housing mounts a tubular metal support sleeve, and a metal drill bur is adapted to be inserted into the sleeve so that the inner end of the bur rotatably and releaseably engages the chuck. To provide for the concentric rotation of the bur within the support sleeve, the shank of the bur incorporates an integral cylindrical metal bearing surface which has a diameter greater than the remaining portion of the shank, but which is somewhat less than the internal diameter of the bore of the support sleeve. The tolerance or spacing between the bearing surface of the shank and the internal bore of the support sleeve is relatively loose, in order to avoid the development of excessive heat from the metal to metal contact between the bearing and the support sleeve during the high speed rotation of the bur. This required spacing between the bearing surface and the bore of the support sleeve is disadvantageous however, since it renders precise control of the surgical operation difficult, and since it permits debris resulting from the drilling operation to move between the bearing surface and bore of the sleeve and into the interior of the sleeve. This in turn can result in contamination, which is difficult to remove, and it can also result in the scoring of the bearing surface of the bur.

It is also common for the burs of such surgical drills to be provided with cutting tips of a variety of configurations and sizes, so that a properly designed cutting tip may be selected in accordance with the particular procedure to be performed. However, since the cutting tips are very small, it is difficult for a surgeon to identify a desired bur, particularly when the bur is mounted in the handpiece.

It is accordingly an object of the present invention to provide a surgical drill and bur for use therewith, and which effectively overcomes the above noted disadvantages and limitations of the prior art devices.

It is a more particular object of the present invention to provide a surgical drill and bur of the described type, and wherein the tolerance between the bearing surface of the bur and the bore of the support sleeve is sufficiently close so as to provide a seal therebetween which prevents the passage of debris past the bearing surface and into the support sleeve, and while maintaining the generation of frictional heat within acceptable limits.

It is also an object of the present invention to provide a surgical drill and bur of the described type, and wherein the bur includes provision for the ready identification of the configuration of size of the cutting tip.

SUMMARY OF THE INVENTION

These and other objects and advantages of the present invention are achieved in the embodiment illustrated herein by the provision of a surgical drill bur which comprises an elongate metal shaft, with the shaft having one end thereof adapted for rotatable interconnection to the chuck of the surgical drill, and an opposite end which mounts the cutting tip. An annular recess is formed in the shaft adjacent but spaced from the opposite end thereof, so as to define a cylindrical journal, and a relatively hard, plastic sleeve bearing is disposed coaxially upon the journal. Preferably, the plastic sleeve bearing has a distinctive color which is correlated to the particular configuration or size of the cutting tip, to thereby facilitate its identification by the surgeon.

It is also preferred that the elongate shaft be composed of first and second shaft components, with the first component having one end thereof adapted for rotatable interconnection to the chuck of the surgical drill, and an opposite end portion in the form of a cylindrical journal. The first shaft component also includes a radial shoulder positioned between the journal and the remainder of the first shaft component, with the radial shoulder facing toward the journal. The second shaft component has a coaxial bore in one end thereof which is coaxially and fixedly mounted upon a portion of the axial length of the cylindrical journal, and such that the one end of the second shaft component forms a second radial shoulder which faces the shoulder of the first shaft component. The plastic sleeve bearing is disposed coaxially upon the remaining portion of the journal, and with the opposite ends of the sleeve bearing disposed adjacent respective ones of the shoulders. Further, the portion of the second shaft component which is immediately adjacent the sleeve bearing has a diameter which is substantially the same as that of the sleeve bearing.

The plastic sleeve bearing is preferably mounted so as to be freely rotatable on the journal of the bur shaft, and when the bur is assembled to a drill of the type comprising a housing for the drive motor and an elongate tubular support sleeve fixedly mounted at one end of the housing, the plastic sleeve bearing preferably contacts the bore of the support sleeve to provide an effective seal therebetween, and so that the relative rotation occurs essentially only between the shaft journal and the bearing during operation, and not between the bearing and the bore of the support sleeve, to thereby minimize the generation of heat. Also, the drill bur is sized such that a portion of the colored plastic sleeve extends beyond the free end of the support sleeve and is visible to the user during use of the instrument, and by reason of the distinctive color of the visible portion of the plastic sleeve, an immediate identification of the particular configuration or size of the cutting tip of the bur can be determined.

As a further aspect of the present invention, a plurality of drill burs may be supplied in a kit form, with each of the cutting tips being of different configuration or size as compared to the cutting tips of the other burs within the kit. Also, each of the plastic sleeves is of a color different from the colors of the sleeves of each of the other burs within the kit, and such that the color of the sleeve permits the ready identification of the configuration of size of the cutting tip of each bur.

BRIEF DESCRIPTION OF THE DRAWINGS

Some of the objects and advantages of the present invention having been stated, others will appear as the description proceeds, when taken in conjunction with the accompanying drawings, in which FIG. 1 is a fragmentary perspective view illustrating a surgical drill which embodies the present invention, and which is shown in association with a conventional guide cannula;

FIG. 2 is a perspective view of the surgical drill;

FIG. 3 is an enlarged fragmentary sectional view of the forward portion of the drill;

FIG. 4 is a sectional view taken substantially along the line 4—4 of FIG. 3;

FIG. 5 is a plan view of a plurality of burs which embody the present invention; and FIG. 6 is an enlarged perspective view of the sleeve bearings of the burs shown in FIG. 5, and illustrating the different colors thereof.

DETAILED DESCRIPTION OF A PREFERRED EMBODIMENT

Referring more particularly to the drawings, FIGS. 1-3 illustrate a surgical instrument which embodies the features of the present invention, and which comprises a drill 10, and a drill bur 12 which is releasably mounted to the drill. The drill 10 includes an elongate cylindrical housing 14, which is sized so as to be easily held in one hand by the surgeon in the manner illustrated in FIG. 1, and the rear portion of the housing mounts an electric motor 15. A power cord 16 for the motor 15 extends from the housing and terminates in an electrical plug 17, which is adapted to be connected to a conventional foot pedal switch (not shown) which permits the surgeon to control the speed of operation of the motor. The motor 15 drives an output coupler 18 which is rotatably mounted in the housing by a bearing 19, and the coupler includes a cylindrical bore 20 having a transverse drive slot at the inner end thereof.

The housing 14 includes a cylindrical internal chamber 22 positioned forwardly of the motor, and a bur locking device is mounted within the internal chamber 22. More particularly, the bur locking device comprises a cylindrical tube 24 having an internal bore 25, and a spring 26 along one side for biasing the tube laterally to the left as seen in FIG. 3. Also, a release pin 28 extends radially through the wall of the housing and is fixed to the tube, such that upon pressing the pin 28 inwardly, the tube may be moved to the right against the force of the spring 26. Also, the end of the tube adjacent the coupler 18 rotatably mounts an annular ring 30 which is aligned with the bore of the tube, and the entrance to the bore at the opposite end of the tube includes a conical guide surface 31.

The drill 10 also includes an elongate tubular support sleeve 33 which is fixedly mounted at the forward end of the housing, and the support sleeve 33 includes an internal cylindrical bore 34 and a free end 35. The tubular support sleeve is preferably fabricated of stainless steel, and it is angled slightly along its length and as seen in FIG. 2, so that the line of sight of a surgeon sighting in a direction generally along the outer end portion of the support sleeve, such as during stapes surgery, will not be obstructed by the housing.

In the illustrated embodiment, the drill bur 12 comprises an elongate shaft composed of first and second components 38 and 39 respectively, both of which are preferably fabricated from stainless steel. The first component 38 includes a cylindrical head 40 at one end thereof, and the head includes a projecting transverse lip 41. The head and lip are sized so as to be adapted to be closely received in the bore 20 and drive slot of the coupler 18 in the manner shown in FIG. 3.

The opposite end of the first shaft component 38 includes a cylindrical journal 42, and a radial shoulder 43 is formed between the journal and the remainder of the component 38, with the radial shoulder 43 facing outwardly toward the journal 42. The remainder of the first shaft component 38, i.e. the portion between the radial shoulder 43 and the head 40, includes a smoothly tapered portion 45 immediately adjacent the shoulder 43, and a reduced diameter portion 46 which extends along a substantial portion of the length of the component 38 and which has a diameter substantially less than the diameter of the radial shoulder, and so as to impart substantial flexibility to the shaft component 38. As a typical example, the diameter of the journal 42 may be about 0.045 inches, the diameter of the shoulder may be about 0.058 inches, and the diameter of the reduced diameter portion 46 may be about 0.020 inches. The overall length of the bur is usually about 3 inches.

The second shaft component 39 includes one end 48 having a coaxial bore 49 which is coaxially and fixedly mounted upon a portion of the axial length of the cylindrical journal 42. Thus the end 48 of the second shaft component 39 forms a second radial shoulder which faces the first radial shoulder 43, and so as to define a recess therebetween. The second component 39 may be fixed on the journal 42 by means of a conventional high strength adhesive which is able to withstand autoclaving temperatures to about 300° F.

A cutting tip 50 is mounted at the opposite end of the second component 39, and the portion 51 of the component 39 adjacent the end 48 is in the form of a cylindrical outer surface. As will be understood by those skilled in the art, the cutting tip 50 may take one of a variety of configurations and sizes, and it may for example take the form of a plate-like circular drill as illustrated in FIG. 3, or the form of a roughened spherical ball ranging in diameter from about 0.5 mm to 2.3 mm, and which may be formed of carbide metal or diamond impregnated metal. The particular cutting tip to by employed is selected to most effectively carry out the operation being performed.

The drill bur 12 also includes a relatively hard, plastic sleeve bearing 52 disposed coaxially upon the journal, with the sleeve bearing 52 having opposite ends which are disposed adjacent respective ones of the radial shoulders 43, 48. A preferred plastic material for the bearing 52 is polytetrafluroethylene sold under the trademark "Teflon" by DuPont. Also, the plastic has a distinctive color which is correlated to the particular configuration or size of the cutting tip, to thereby facilitate its identification. The outer diameter of the bearing 52 is typically about 0.060 inches and preferably is substantially the same as the diameter of the bore 34 of the support sleeve 33, and such that the outer periphery of the bearing contacts the bore of the sleeve to provide an effective seal therebetween. Also, the bore in the bearing 52 is sized to permit the journal 42 to freely rotate within the bore of the bearing 52. The outer diameter of the bearing 52 is also about the same as the diameter of the adjacent portion 51 of the second shaft component.

When the drill bur 12 is assembled to the drill 10 in the manner shown in FIG. 3, the head 40 is received in the coupler 18, and a portion of the axial length of the sleeve bearing 52 extends outwardly beyond the free end of the support sleeve, as seen at 54, and so as to be readily visible to the surgeon. Since the color of the bearing 52 is correlated to the particular configuration or size of the cutting tip 50, the surgeon may readily determine the particular configuration or size of the cutting tip being employed during its use.

In its assembled condition, the annular ring 30 on the tube 24 engages the adjacent end of the head 40 of the bur, to prevent its longitudinal withdrawal. When disassembly is desired, the pin 28 is pressed inwardly, so as to center the tube 24 in the chamber 22 and thereby align the opening of the ring 30 and the bore 25 of the tube 24 with the head 40, and so that the head may be freely withdrawn therethrough. To assemble a different bur, the pin 28 is depressed and the head end is inserted through the support sleeve and the tube 24 and until it is received in the bore of the coupler 18. The pin 28 is then released so that the spring 26 moves the tube 24 to a laterally offset position and locks the bur in the assembled position.

In operation, the motor 15 serves to rotate the bur 12 at a high rotational speed, and the contact between the outer diameter of the bearing 52 and the bore 34 of the support sleeve 33 serves to hold the bearing 52 against significant rotation, although some small amount of rotation by the bearing 52 is possible. Thus essentially all of the relative rotation occurs between the journal 42 and the bore of the bearing 52, to thereby minimize the generation of heat and also provide an effective seal between the bearing 52 and bore 34 of the support sleeve 33.

Drill burs 12 of the present invention are conventionally provided in kit form, and wherein the kit is composed of a plurality of drill burs, with each of the cutting tips 50 of the burs being of a different configuration or size as compared to the cutting tips of the other burs within the kit. Also, each of the plastic sleeve bearings 52 of the various burs in the kit includes a color indicium which is different from the color indicium of the sleeve bearings of the other burs within the kit. Thus the color indicium of each sleeve bearing 52 permits the ready identification of the configuration or size of the cutting tip of each bur.

The color indicium may take the form of different solid colors, as illustrated in FIG. 6, or they may take the form of a combination of colors and strips. Thus for example, the presence of a stripe may indicate a particular type of cutting tip. As a more specific example, the bearing 52 of a 0.5 mm diameter carbide cutting tip may be a solid color, and the bearing of a 0.5 mm diamond cutting tip may have the same color with a white stripe.

In the drawings and specification, a preferred embodiment of the invention has been illustrated and described, and although specific terms are employed, they are used in a generic and descriptive sense and not for purposes of limitation.

We claim:

1. A drill bur for use with a surgical drill having a rotatably driven chuck, said drill bur comprising
   an elongate shaft composed of first and second shaft components, said first component having one end thereof adapted for rotatable interconnection of the chuck of the surgical drill and an opposite end portion in the form of a cylindrical journal, and a first radial shoulder positioned between said journal and the remainder of said first shaft component, with said first radial shoulder facing toward said journal, and wherein said second shaft component has a coaxial bore in one end thereof which is coaxially and fixedly mounted upon a portion of the axial length of said cylindrical journal, and such that said one end of said second shaft component forms a second radial shoulder which faces said first radial shoulder, and a cutting tip mounted at the other end of said second shaft component, and
   a relatively hard, plastic sleeve bearing disposed coaxially upon said journal with said sleeve bearing having opposite ends which are disposed adjacent respective ones of said radial shoulders, and with said plastic sleeve bearing being freely rotatable with respect to said journal, and with the portion of said second shaft component adjacent said sleeve bearing having a cylindrical outer surface which has an outer diameter which is substantially the same as that of said sleeve bearing.
   said plastic sleeve bearing being distinctively colored, with the color being correlated to the particular configuration or size of said cutting tip.

2. The drill bur as defined in claim 1 wherein said remainder of said first shaft component includes a reduced diameter portion along a substantial portion of the length thereof and which has a diameter substantially less than the diameter of said first radial shoulder and so as to impart substantial flexibility to said first shaft component.

3. A kit composed of a plurality of drill burs, with each of said burs being adapted to be selectively used in combination with a surgical drill, and with each bur comprising
   (a) an elongate shaft composed of first and second shaft components, said first component having one end thereof adapted for rotatable interconnection to the chuck of the surgical drill and an opposite end portion in the form of a cylindrical journal, and a first radial shoulder positioned between said journal and the remainder of said first shaft component, with said first radial shoulder facing toward said journal, and wherein said second shaft component has a coaxial bore in one end thereof which is coaxially and fixedly mounted upon a portion of the axial length of said cylindrical journal, and such that said one end of said second shaft component forms a second radial shoulder which faces said first radial shoulder,
   (b) a relatively hard plastic sleeve bearing disposed coaxially upon said journal with said sleeve bearing having opposite ends which are disposed adjacent respective ones of said radial shoulders, with said plastic sleeve bearing being freely rotatable with respect to said journal, and with the portion of said second shaft component adjacent said sleeve bearing having a cylindrical outer surface which has an outer diameter which is substantially the same as that of said sleeve bearing,
   (c) a cutting tip mounted at the other end of said second shaft component,
   each of said cutting tips of said burs being of a different configuration or size as compared to the cutting tips of the other burs within said kit, and each of said plastic sleeve bearings including a color indicium which is different from the color indicium of the sleeve bearings of each of the other burs within said kit, and such that the color indicium of the sleeve bearing permits the ready identification of the configuration or size of the cutting tip of each bur.

4. A surgical instrument comprising
   a drill comprising a housing, a chuck rotatably mounted in said housing, drive means for rotating said chuck, and an elongate tubular support sleeve fixedly mounted at one end of said housing, and with said support sleeve having an internal cylindrical bore and a free opposite said housing, a drill bur releaseably and coaxially mounted within said bore of said support sleeve and including (a) an elongate shaft, said shaft having one end thereof releaseably and rotatably connected to said chuck, an opposite outer end positioned outside of said free end of said support sleeve, and an annular recess adjacent but spaced from said outer end and so as to define a cylindrical journal, and with said journal extending along a portion of the axial length of said support sleeve adjacent said free end thereof and outwardly beyond said free end of said support sleeve, (b) a relatively hard, plastic sleeve bearing disposed coaxially upon said journal, and such that a portion of the axial length of said sleeve bearing is disposed within said support sleeve and a portion of the axial length of said sleeve bearing extends outwardly beyond said free end of said support so as to be readily visible to the user, and (c) a cutting tip mounted at said outter end of said shaft, said plastic sleeve bearing being distinctively colored, with the color being correlated to the particular configuration or size of said cutting tip, and whereby the distinctive color of said sleeve bearing is visible to the user during use of the instrument and may be used to readily identify a particular configuration or size of said cutting tip.

5. The surgical instrument as defined in claim 4 wherein said plastic sleeve bearing is freely rotatable upon said journal, and wherein said internal bore of said support sleeve has a predetermined diameter, and said plastic sleeve bearing has an outer diameter which is substantially the same as the predetermined diameter of said bore, so as to provide a seal between said bearing and said internal bore which effectively prevents the passage of debris into said support sleeve and while permitting free rotation between said journal of said shaft and said bearing.

6. A surgical instrument comprising a drill comprising a housing, a chuck rotatably mounted in said housing, drive means for rotating said chuck, and an elongate tubular support sleeve fixedly mounted at one end of said housing, and with said support sleeve having an internal cylindrical bore having a predetermined internal diameter, a drill bur releasably and coaxially mounted within said bore of said support sleeve and including (a) an elongate shaft composed of first and second shaft components, said first component having one end thereof releasably and rotatably interconnected to the chuck of the surgical drill and an opposite end portion in the form of a cylindrical journal, and a first radial shoulder positioned between said journal and the remainder of said first shaft component, with said first radial shoulder facing toward said journal, and wherein said second shaft component has a coaxial bore in one end thereof which is coaxially and fixedly mounted upon a portion of the axial length of said cylindrical journal, and such that said one end of said second shaft component forms a second radial shoulder which faces said first radial shoulder, (b) a relatively hard, plastic sleeve bearing disposed coaxially upon said journal, with said sleeve bearing having opposite ends which are disposed adjacent respective ones of said radial shoulders, and with said plastic sleeve bearing being freely rotatable with respect to said journal, and with at least a portion of the axial length of said sleeve bearing being disposed within said support sleeve, the portion of said second shaft component adjacent said sleeve bearing having a cylindrical outer surface which has an outer diameter which is substantially the same as that of said sleeve bearing, said plastic sleeve bearing having an outer diameter which is substantially the same as said predetermined internal diameter of said bore so as to provide a seal between said bearing and said internal bore which effectively prevents the passage of debris into said support sleeve and while permitting free rotation between said journal of said shaft and said bearing, and (c) a cutting tip mounted at the other end of said second shaft component and exteriorly of said support sleeve.

said plastic sleeve bearing being distinctively colored, with the color being correlated to the particular configuration or size of said cutting tip.

7. The surgical instrument as defined in claim 6 wherein said first shaft component is elongate and readily flexible.

* * * * *